US012721602B2

(12) United States Patent
Azizian

(10) Patent No.: US 12,721,602 B2
(45) **Date of Patent: *Sep. 1, 2026**

(54) MULTI-DIMENSIONAL VISUALIZATION IN COMPUTER-ASSISTED TELE-OPERATED SURGERY

(71) Applicant: INTUITIVE SURGICAL OPERATIONS, INC., Sunnyvale, CA (US)

(72) Inventor: Mahdi Azizian, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 202 days.

This patent is subject to a terminal disclaimer.

(21) Appl. No.: 18/420,428

(22) Filed: Jan. 23, 2024

(65) Prior Publication Data

US 2024/0156548 A1 May 16, 2024

Related U.S. Application Data

(63) Continuation of application No. 16/481,196, filed as application No. PCT/US2018/018156 on Feb. 14, 2018, now Pat. No. 11,918,306.

(Continued)

(51) Int. Cl.
*A61B 34/00* (2016.01)
*A61B 34/35* (2016.01)

(Continued)

(52) U.S. Cl.
CPC .............. *A61B 34/25* (2016.02); *A61B 90/37* (2016.02); *G06T 11/60* (2013.01); *A61B 34/35* (2016.02);

(Continued)

(58) Field of Classification Search
None
See application file for complete search history.

(56) References Cited

U.S. PATENT DOCUMENTS 5,808,665 A 9/1998 Green et al.
6,628,977 B2 9/2003 Graumann et al.

(Continued)

FOREIGN PATENT DOCUMENTS

CN 103948432 A 7/2014
CN 104411248 A 3/2015

(Continued)

OTHER PUBLICATIONS

Extended European Search Report for Application No. EP18754256.8 mailed on Oct. 27, 2020, 8 pages.

(Continued)

*Primary Examiner* — Peter Hoang
(74) *Attorney, Agent, or Firm* — Artegis Law Group, LLP

(57) ABSTRACT

Techniques for multi-dimensional visualization in computer-assisted teleoperated surgery include a display device and one or more processing devices. The one or more processing devices are configured to receive 2D images of a human body, wherein the 2D images include images acquired using at least two different imaging modalities; display a first image of the 2D images on the display device in accordance with location information associated with the first image, the first image being acquired using a first imaging modality; and display a second image and a third image of the 2D images. The second and third images are overlaid on and registered with respect to the first image in accordance with the location information associated with the second and third images. The second and third images are (Continued)

acquired using a second imaging modality. The second and third images are displayed together for at least a period of time.

20 Claims, 9 Drawing Sheets

Related U.S. Application Data

(60) Provisional application No. 62/458,722, filed on Feb. 14, 2017.

(51) Int. Cl.
*A61B 90/00* (2016.01)
*G06T 11/60* (2026.01)

(52) U.S. Cl.
CPC ... *A61B 2090/367* (2016.02); *A61B 2090/371* (2016.02); *A61B 2090/373* (2016.02); *A61B 2090/374* (2016.02); *A61B 2090/3762* (2016.02); *A61B 2090/378* (2016.02); *G06T 2210/41* (2013.01)

(56) References Cited

U.S. PATENT DOCUMENTS

| | | | |
|---|---|---|---|
| 6,714,839 | B2 | 3/2004 | Salisbury, Jr. et al. |
| 8,364,242 | B2 | 1/2013 | Li |
| 11,918,306 | B2 | 3/2024 | Azizian |
| 2007/0167806 | A1 | 7/2007 | Wood et al. |
| 2008/0008366 | A1 | 1/2008 | Desh et al. |
| 2009/0149977 | A1 | 6/2009 | Schendel |
| 2011/0102549 | A1 | 5/2011 | Takahashi |
| 2011/0141140 | A1 | 6/2011 | Duhamel et al. |
| 2014/0051922 | A1 | 2/2014 | Guthart et al. |
| 2014/0303491 | A1 | 10/2014 | Shekhar et al. |
| 2015/0182191 | A1* | 7/2015 | Caluser ................ A61B 8/5246 600/407 |
| 2016/0381256 | A1 | 12/2016 | Aguirre-Valencia |
| 2017/0186200 | A1 | 6/2017 | Utsunomiya |
| 2019/0388162 | A1 | 12/2019 | Azizian |

FOREIGN PATENT DOCUMENTS

| | | | |
|---|---|---|---|
| CN | 106030656 | A | 10/2016 |
| CN | 106163408 | A | 11/2016 |
| EP | 3114997 | A1 | 1/2017 |
| WO | WO-2007047782 | A2 | 4/2007 |
| WO | WO-2015136392 | A1 | 9/2015 |

OTHER PUBLICATIONS

International Preliminary Report on Patentability for Application No. PCT/US2018/018156, mailed on Aug. 29, 2019, 11 pages.
International Search Report and Written Opinion for Application No. PCT/US2018/018156, mailed on Jun. 25, 2018, 12 pages.
Office Action for Chinese Application No. CN20188011560, mailed May 7, 2022, 30 pages.
Office Action for CN Application No. 201880011560.3, mailed Jul. 27, 2023, 32 pages.
Office Action for CN Application No. 201880011560.3, mailed Mar. 29, 2023, 26 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Extended European Search Report for Application No. EP26156625.1, mailed on Apr. 29, 2026, 8 pages.

* cited by examiner

400

460
450

MULTI-DIMENSIONAL VISUALIZATION IN COMPUTER-ASSISTED TELE-OPERATED SURGERY

CROSS-REFERENCES TO RELATED APPLICATIONS

This application is a continuation of U.S. patent application Ser. No. 16/481,196, filed Jul. 26, 2019, which is a U.S. National Stage Application of International Patent Application No. PCT/US2018/018156, filed Feb. 14, 2018, which claims the benefit of U.S. Provisional Application No. 62/458,722, filed Feb. 14, 2017. The disclosures of these prior applications are hereby incorporated by reference in their entirety.

TECHNICAL FIELD

This disclosure relates to devices and methods for minimally invasive computer-assisted tele-operated surgery.

BACKGROUND

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. The surgeon performs the surgical procedures on the patient by manipulating master control input devices, which in turn control the motion of robotic instruments.

SUMMARY

In one aspect, this document features a method of displaying images of portions of a human body on a display device. The method includes receiving a representation of a plurality of images of the portions of the human body, wherein the plurality of images includes images of at least two different modalities, and the representation includes location information corresponding to at least a subset of the plurality of images. The method also includes displaying a first image of the plurality of images on the display device in accordance with corresponding location information associated with the first image, the first image being of a first modality, and displaying a second image of the plurality of images, the second image overlaid on the first image in accordance with corresponding location information associated with the second image, the second image being of a second modality. The method further includes displaying at least a third image of the plurality of images, the third image overlaid on the first image in accordance with corresponding location information associated with the third image. The third image is of the second modality, and the second and third images are displayed concurrently for at least a period of time.

In another aspect, this document features a surgical system that includes a display device, and one or more processing devices. The one or more processing devices are configured to operate the surgical system to perform a surgical process, and receive a representation of a plurality of images of the portions of the human body. The plurality of images includes images of at least two different modalities, and the representation includes location information corresponding to at least a subset of the plurality of images. The one or more processing devices are also configured to display a first image of the plurality of images on the display device in accordance with corresponding location information associated with the first image, wherein the first image is of a first modality. The one or more processing devices are further configured to display a second image of the plurality of images, the second image overlaid on the first image in accordance with corresponding location information associated with the second image, the second image being of a second modality, and display at least a third image of the plurality of image. The third image is overlaid on the first image in accordance with corresponding location information associated with the third image, and the third image is of the second modality. The second and third images are displayed concurrently for at least a period of time.

In another aspect, this document features one or more machine-readable non-transitory storage devices encoded with machine-readable instructions configured to cause one or more processing devices to perform various operations. The operations include receiving a representation of a plurality of images of the portions of the human body, wherein the plurality of images includes images of at least two different modalities, and the representation includes location information corresponding to at least a subset of the plurality of images. The operations also include displaying a first image of the plurality of images on the display device in accordance with corresponding location information associated with the first image, the first image being of a first modality, and displaying a second image of the plurality of images, the second image overlaid on the first image in accordance with corresponding location information associated with the second image, the second image being of a second modality. The operations further include displaying at least a third image of the plurality of images, wherein the third image is overlaid on the first image in accordance with corresponding location information associated with the third image. The third image is of the second modality, and the second and third images are displayed concurrently for at least a period of time.

In another aspect, this document features a method of providing visual feedback during a surgical process on a display device. The method includes displaying a first image of a first modality on the display device in accordance with location information associated with the first image, the first image representing a body part at which the surgical process is being carried out. The method includes displaying a set of multiple images of a second modality, the set representing at least a portion of the body part, and being overlaid on the first image in accordance with corresponding location information associated with each image of the set. At least two of the images from the set are displayed concurrently for at least a period of time. The method also includes receiving user-input associated with the surgical process in response to displaying the set of multiple images overlaid on the first image. A robotically controllable surgical instrument can be operated based on the user-input.

In another aspect, this document features a surgical system that includes a display device, one or more processing devices, and one or more input devices. The one or more processing devices are configured to operate the surgical system to perform a surgical process, and display a first image of a first modality on the display device in accordance with location information associated with the first image. The first image represents a body part at which the surgical process is being carried out. The one or more processing devices are also configured to display a set of multiple images of a second modality, the set representing at least a portion of the body part, and being overlaid on the first image in accordance with corresponding location information associated with each image of the set. At least two of the images from the set are displayed concurrently for at least a period of time. The one or more input devices are configured to receive user-input associated with the surgical process in response to displaying the set of multiple images overlaid on the first image. A robotically controllable surgical instrument can be operated based on the user-input.

In another aspect, this document features one or more machine-readable non-transitory storage devices encoded with machine-readable instructions configured to cause one or more processing devices to perform various operations. The operations include displaying a first image of a first modality on the display device in accordance with location information associated with the first image, the first image representing a body part at which the surgical process is being carried out. The operations also include displaying a set of multiple images of a second modality, the set representing at least a portion of the body part, and being overlaid on the first image in accordance with corresponding location information associated with each image of the set. At least two of the images from the set are displayed concurrently for at least a period of time. The operations further include receiving user-input associated with the surgical process in response to displaying the set of multiple images overlaid on the first image. A robotically controllable surgical instrument can be operated based on the user-input.

Implementations of the above aspects can include one or more of the following features. The first image can be displayed in a hidden mode such that the first image is not visible. The first image can be a two-dimensional (2D) B-mode ultrasound image, and the second and third images can be 2D Doppler ultrasound images. The first image can be an endoscopic image, and the second and third images can be ultrasound images. The second and third images can be two-dimensional images, which when displayed concurrently in accordance with corresponding location information, provide a three-dimensional (3D) visualization of the portions of the human body on the display device. The second image and the at least third image can be acquired by a probe of an imaging device traversing a trajectory within the body part. At least one of the two different modalities can include live images, and the other of the two different modalities can include images acquired using at least one of: an endoscope, an ultrasound imaging device, a computed tomography (CT) imaging device, a Positron Emission Tomography-CT (PET-CT) imaging device, a Single-Photon Emission CT (SPECT) imaging device, a Magnetic Resonance Imaging (MRI) device or a Cone-beam CT (CBCT) imaging device. The live images can include images acquired using at least one of: an endoscope, or an ultrasound imaging device. The location information can include geo-tagging information with respect to a common coordinate system. The second and third images can be registered with respect to the first image. The first, second and third images can be registered with respect to a common reference coordinate system. The second and third images can represent images acquired at two different time points. A new image may be displayed on the display device in place of the first image, and responsive to detecting that the new image is being displayed, the display of the second and third images can be adjusted in accordance with location information associated with the new image. Adjusting the display of the second and third images can include registering the second and third images with respect to the new image.

Some or all of the embodiments described herein may provide one or more of the following advantages. In some cases, a three dimensional (3D) visualization of a surgical site can be provided by concurrently displaying a series of two-dimensional (2D) images spatially registered with respect to a common coordinate system. This may allow for a three-dimensional visualization to be rendered without using computationally complex and potentially time-consuming 3D reconstruction processes that may introduce undesirable latencies. In addition, 3D perception may be provided using modalities such as ultrasound images captured using ultrasound probes, which in turn may allow for better visualization of anatomical structures, tumors etc. during minimally invasive surgeries (MIS). In some case, by displaying a series of two-dimensional (2D) Doppler ultrasound images in order, but leaving a trace of an earlier image on the display device, a better visualization of temporal events such as tissue perfusion, blood flow etc. may be provided during MIS.

DETAILED DESCRIPTION

Figure 1:
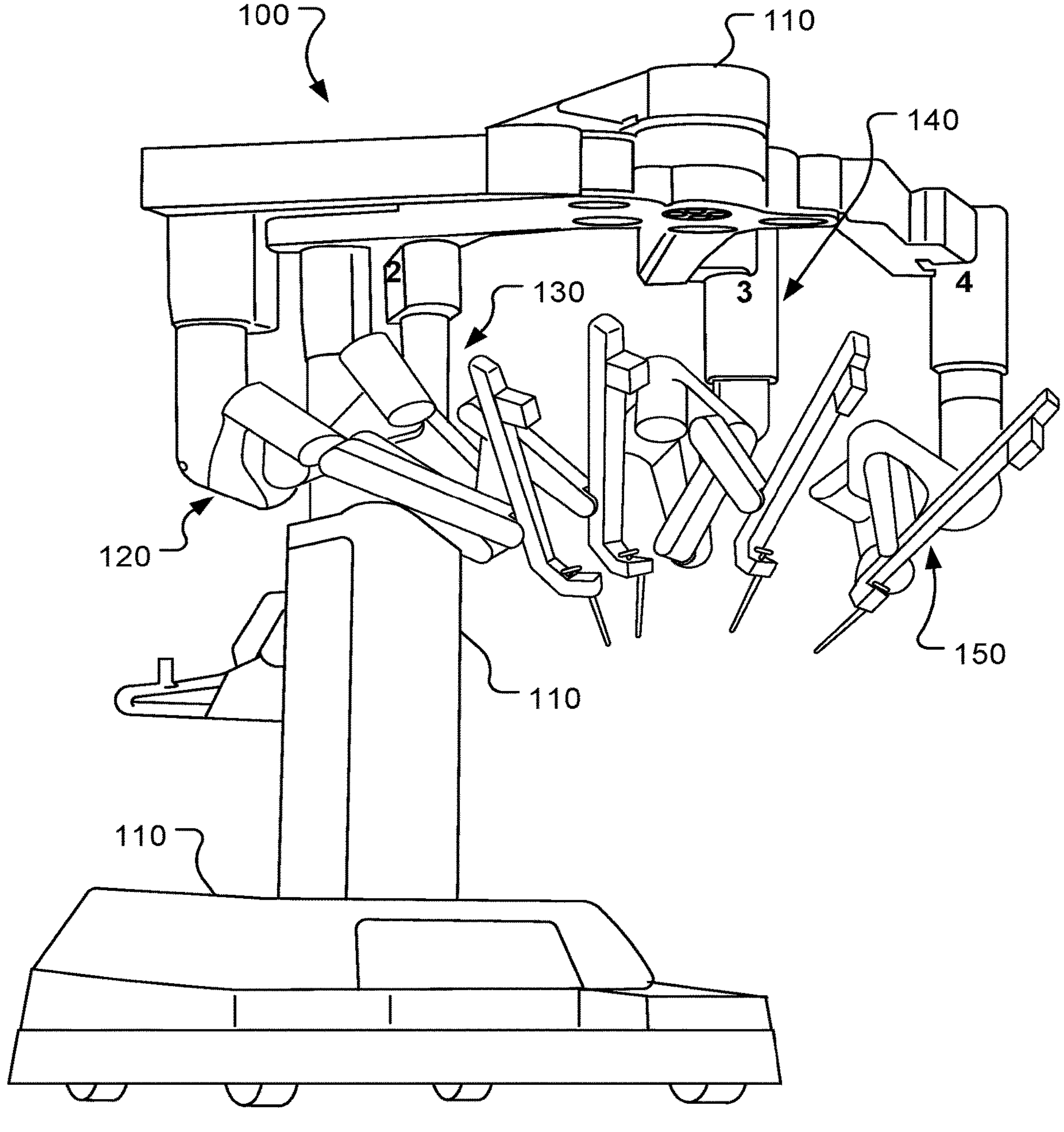
FIG. 1 is a perspective view of an example patient-side cart of a computer-assisted tele-operated surgery system.

This document describes technology that, in some cases, improves visualization of surgical sites and anatomical parts during image-guided surgical processes such as minimally invasive robot-assisted surgery (also referred to herein as minimally invasive surgery (MIS)). For example, multi-dimensional information such as spatial 3D perspectives, or temporal changes can be rendered on a surgeon's console using lower-dimensional data such as 2D images. This may be done, for example, by capturing multiple 2D slices of a 3D structure using an imaging device such as an ultrasound probe, and concurrently displaying the captured slices registered with respect to a common coordinate system. This in turn may allow for implementing 3D visualization without having to employ 3D reconstruction processes that could be computationally intensive as well as time-consuming. In some cases, temporal information such as blood flow through vasculature can also be displayed, for example, by displaying a series of colored Doppler ultrasound images in sequence, wherein at least some of the images in the sequence are displayed concurrently. For example, if a set of Doppler images are displayed sequentially, and the individual images are continued to be displayed until all the images from the set have been displayed, the resulting display can represent temporal information such as tissue perfusion or blood flow for the period of time over which the Doppler images are captured. In some implementations, the 2D images can be displayed registered with respect to one or more images of a different modality. For example, ultrasound images that together represent a 3D structure can be registered with respect to an endoscope image coordinate system such that a surgeon is able to visualize 3D anatomical structures (e.g., tumors, vasculature, etc.) underlying the portions visible in the field of view of the endoscope.

Aspects of the invention are described primarily in terms of an implementation using a da Vinci® Surgical System, commercialized by Intuitive Surgical, Inc. of Sunnyvale, California. Examples of such surgical systems are the da Vinci® Xi™ Surgical System (Model IS4000) and the da Vinci® Si™ HD™ Surgical System (Model IS3000). It should be understood that aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are described for illustrative purposes, and are not to be considered as limiting the scope of the inventive aspects disclosed herein. As applicable, inventive aspects may be embodied and implemented in both relatively smaller, hand-held, hand-operated devices and relatively larger systems that have additional mechanical support, as well as in other embodiments of computer-assisted tele-operated medical devices.

Figure 2:
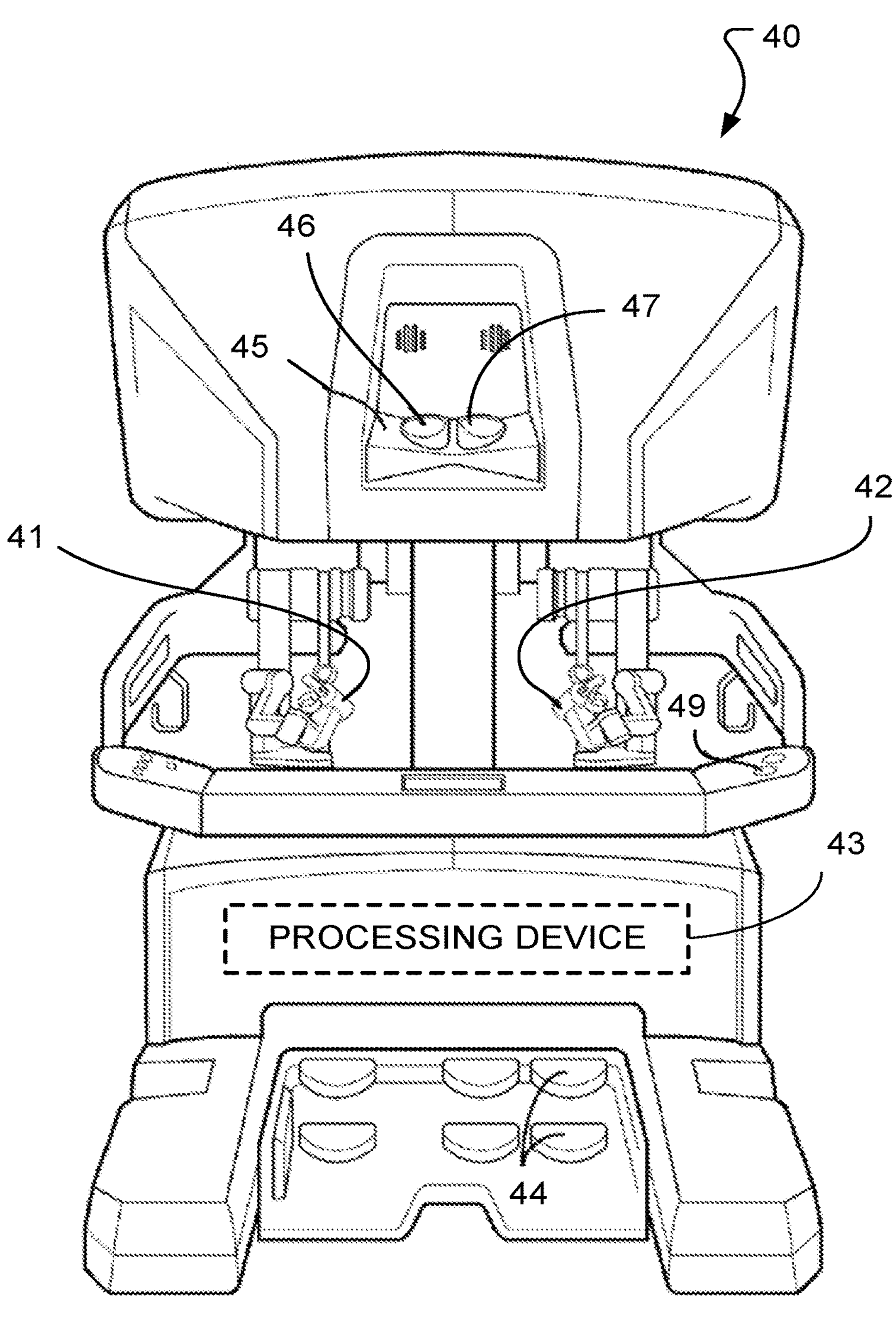
FIG. 2 is a front view of an example surgeon console of a computer-assisted tele-operated surgery system.

Referring to FIGS. 1 and 2, systems for minimally invasive computer-assisted telesurgery (also referred to as MIS) can include a patient-side cart 100 and a surgeon console 40. Telesurgery is a general term for surgical systems where the surgeon uses some form of remote control, e.g., a servomechanism, or the like, to manipulate surgical instrument movements rather than directly holding and moving the instruments by hand. The robotically manipulatable surgical instruments can be inserted through small, minimally invasive surgical apertures to treat tissues at surgical sites within the patient body, avoiding the trauma associated with rather large incisions required for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the patient-side cart 100 includes a base 110, a first robotic manipulator arm assembly 120, a second robotic manipulator arm assembly 130, a third robotic manipulator arm assembly 140, and a fourth robotic manipulator arm assembly 150. Each robotic manipulator arm assembly 120, 130, 140, and 150 is pivotably coupled to the base 110. In some embodiments, fewer than four or more than four robotic manipulator arm assemblies may be included as part of the patient-side cart 100. While in the depicted embodiment the base 110 includes casters to allow ease of mobility, in some embodiments the patient-side cart 100 is fixedly mounted to a floor, ceiling, operating table, structural framework, or the like.

In a typical application, two of the robotic manipulator arm assemblies 120, 130, 140, or 150 hold surgical instruments and a third holds a stereo endoscope. The remaining robotic manipulator arm assembly is available so that a third instrument may be introduced at the work site. Alternatively, the remaining robotic manipulator arm assembly may be used for introducing a second endoscope or another image capturing device, such as an ultrasound transducer, to the work site.

Each of the robotic manipulator arm assemblies 120, 130, 140, and 150 is conventionally formed of links that are coupled together and manipulated through actuatable joints. Each of the robotic manipulator arm assemblies 120, 130, 140, and 150 includes a setup arm and a device manipulator. The setup arm positions its held device so that a pivot point occurs at its entry aperture into the patient. The device manipulator may then manipulate its held device so that it may be pivoted about the pivot point, inserted into and retracted out of the entry aperture, and rotated about its shaft axis.

In the depicted embodiment, the surgeon console 40 includes a stereo vision display 45 so that the user may view the surgical work site in stereo vision from images captured by the stereoscopic camera of the patient-side cart 100. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control the motion of robotic instruments.

The surgeon console 40 also includes left and right input devices 41, 42 that the user may grasp respectively with his/her left and right hands to manipulate devices (e.g., surgical instruments) being held by the robotic manipulator arm assemblies 120, 130, 140, and 150 of the patient-side cart 100 in preferably six or more degrees-of-freedom ("DOF"). Foot pedals 44 with toe and heel controls are provided on the surgeon console 40 so the user may control movement and/or actuation of devices associated with the foot pedals.

A processing device 43 is provided in the surgeon console 40 for control and other purposes. The processing device 43 performs various functions in the medical robotic system. One function performed by processing device 43 is to translate and transfer the mechanical motion of input devices 41, 42 to actuate their corresponding joints in their associated robotic manipulator arm assemblies 120, 130, 140, and 150 so that the surgeon can effectively manipulate devices, such as the surgical instruments. Another function of the processing device 43 is to implement the methods, cross-coupling control logic, and controllers described herein.

The processing device 43 can include one or more processors, digital signal processors (DSPs), field-programmable gate arrays (FPGAs), and/or microcontrollers, and may be implemented as a combination of hardware, software and/or firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processing device 43 may also be distributed as subunits throughout the telesurgery system. One or more of the subunits may be physically remote (e.g., located on a remote server) to the telesurgery system.

Figure 3:
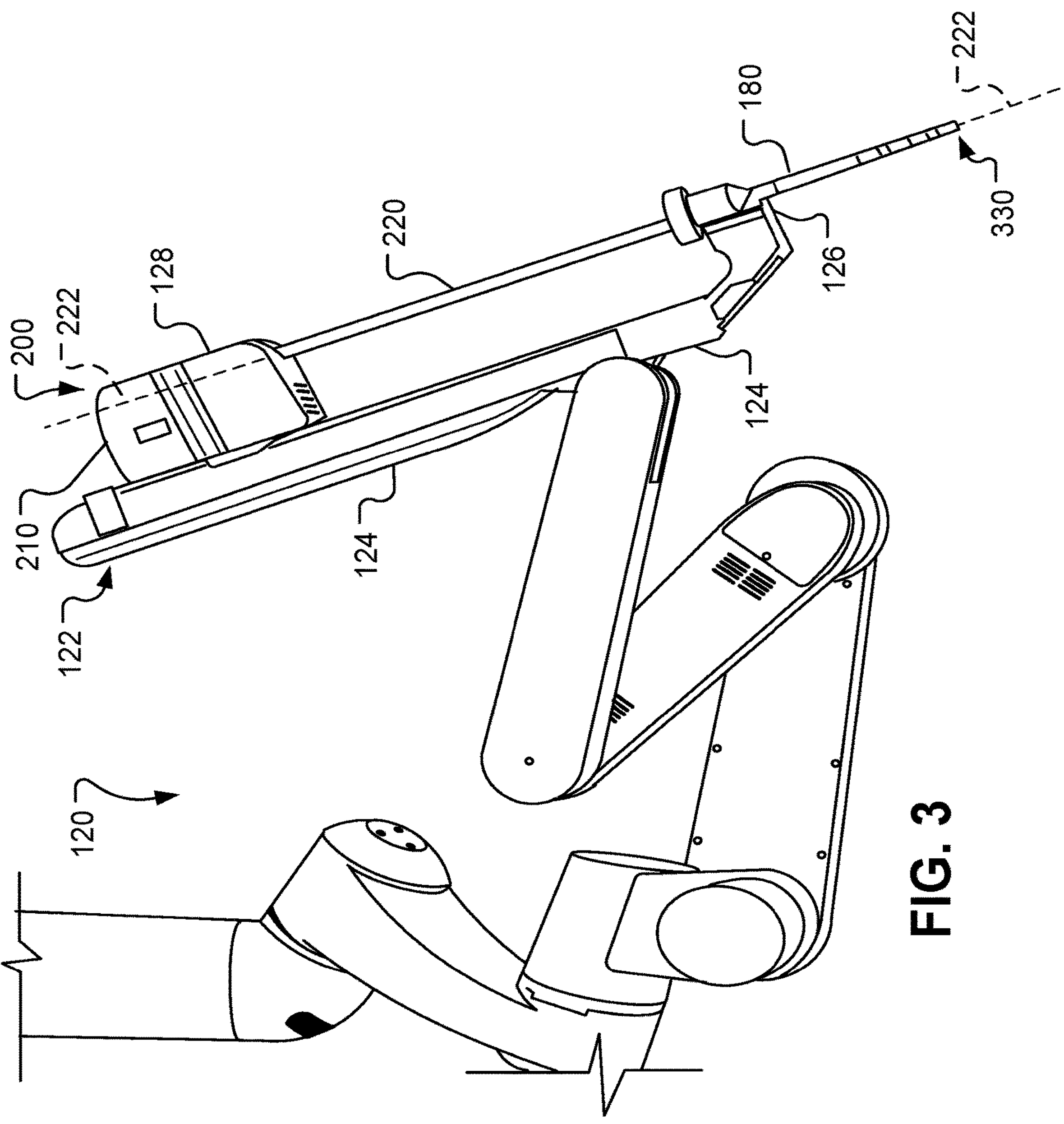
FIG. 3 is a side view of an example robotic manipulator arm assembly of a computer-assisted tele-operated surgery system.

Referring also to FIG. 3, the robotic manipulator arm assemblies 120, 130, 140, and 150 can manipulate devices such as surgical instruments to perform MIS. For example, in the depicted arrangement the robotic manipulator arm assembly 120 is pivotably coupled to an instrument holder 122. A cannula 180 and a surgical instrument 200 are, in turn, releasably coupled to the instrument holder 122. The cannula 180 is a hollow tubular member that is located at the patient interface site during a surgery. The cannula 180 defines a lumen in which an elongate shaft 220 of the surgical instrument 200 is slidably disposed. As described further below, in some embodiments the cannula 180 includes a distal end portion with a body wall retractor member. The instrument holder 122 is pivotably coupled to a distal end of the robotic manipulator arm assembly 120. In some embodiments, the pivotable coupling between the instrument holder 122 and the distal end of robotic manipulator arm assembly 120 is a motorized joint that is actuatable from the surgeon console 40 and processor 43.

The instrument holder 122 includes an instrument holder frame 124, a cannula clamp 126, and an instrument holder carriage 128. In the depicted embodiment, the cannula clamp 126 is fixed to a distal end of the instrument holder frame 124. The cannula clamp 126 can be actuated to couple with, or to uncouple from, the cannula 180. The instrument holder carriage 128 is movably coupled to the instrument holder frame 124. More particularly, the instrument holder carriage 128 is linearly translatable along the instrument holder frame 124. In some embodiments, the movement of the instrument holder carriage 128 along the instrument holder frame 124 is a motorized, translational movement that is actuatable/controllable by the processor 43. The surgical instrument 200 includes a transmission assembly 210, the elongate shaft 220, and an end effector 230. The transmission assembly 210 may be releasably coupled with the instrument holder carriage 128. The shaft 220 extends distally from the transmission assembly 210. The end effector 230 is disposed at a distal end of the shaft 220.

The shaft 220 defines a longitudinal axis 222 that is coincident with a longitudinal axis of the cannula 180. As the instrument holder carriage 128 translates along the instrument holder frame 124, the elongate shaft 220 of the surgical instrument 200 is moved along the longitudinal axis 222. In such a manner, the end effector 230 can be inserted and/or retracted from a surgical workspace within the body of a patient.

Figures 4A, 4B:
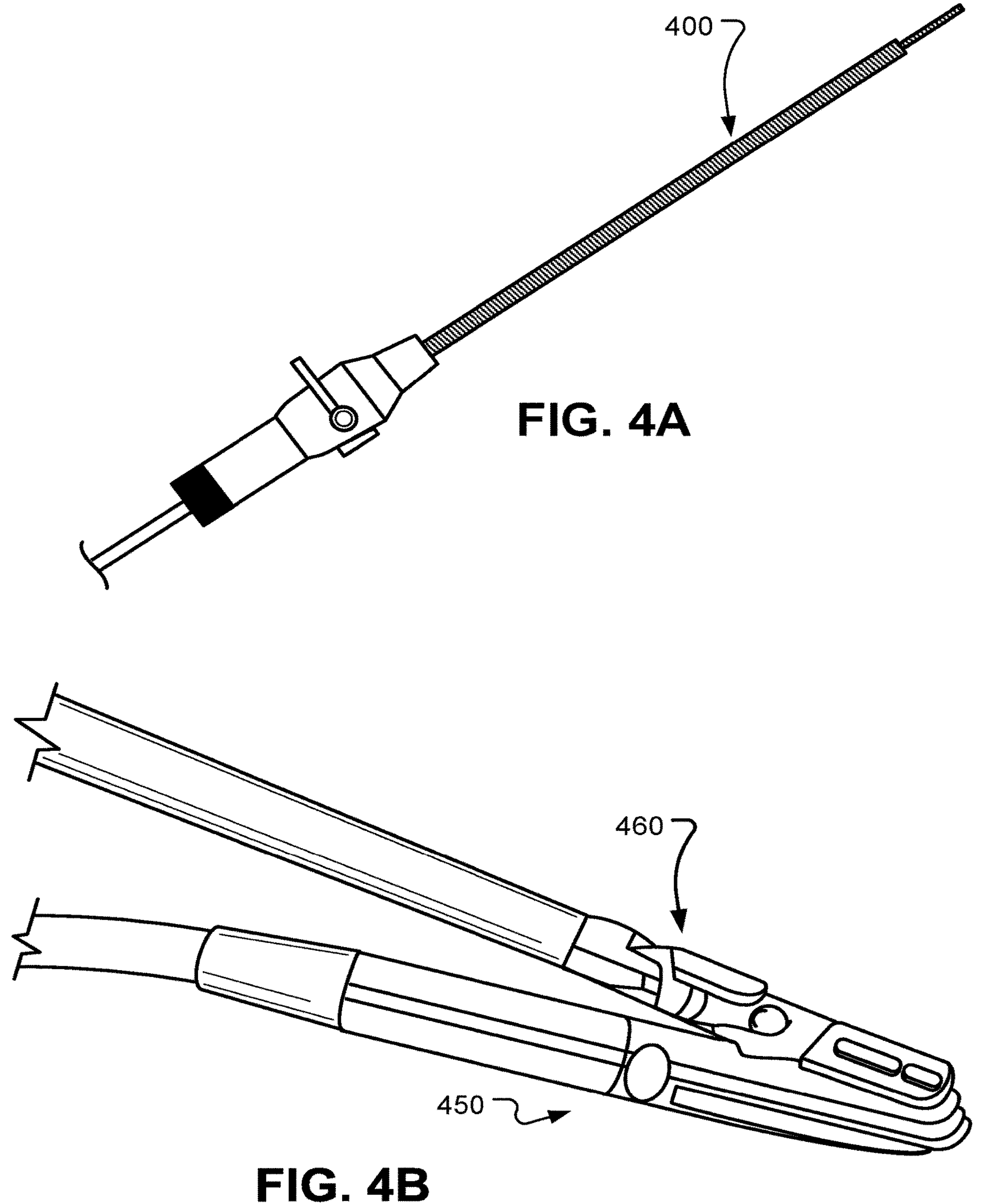
FIG. 4A shows a laparoscopic ultrasound probe.
FIG. 4B shows a drop-in ultrasound probe grasped by a laparoscopic tool.

In some implementations, a robotic manipulator arm assembly 120 can be used to hold and manipulate an ultrasound transducer such as shown in FIGS. 4A and 4B. Specifically, FIG. 4A shows a laparoscopic ultrasound probe 400, and FIG. 4B shows a drop-in ultrasound probe 450 that can be grasped by a laparoscopic tool 460. Ultrasound imaging can be a safe and affordable modality that may be used in robotic image-guided surgeries. For example, ultrasound images can provide intraoperative information about anatomical structures beneath the surface of organs that are visible via an endoscope. In MIS, this may improve visualization for a surgeon, for example, by providing information about underlying anatomical features (e.g., vasculature, bile ducts, ureters etc.) that should not be injured. In some cases, the ultrasound images may also help in visualizing target lesions (e.g., tumors, cysts) that would be removed by the surgeon. Specialized ultrasound images such as Doppler images may be helpful in visualizing temporal information such as blood flow or tissue perfusion.

Despite the benefits of ultrasound images, using the ultrasound modality in MIS can be challenging due to various reasons. For example, because typical ultrasound transducers generate 2D slices, a surgeon may find it challenging to perceive a 3D anatomical structures from the 2D slices. While 3D ultrasound probes do exist, they are often too large to be used in MIS, and/or have unacceptable 3D resolution. When using a 2D probe, the surgeon may try to scan an area by sweeping the 2D probe (e.g., the probe 400 or 450) over the region of interest in trying to get a three dimensional sense of the underlying anatomical structures, a process that may be error-prone and difficult. In addition, the 2D slices may not be aligned with the surgical instruments (e.g., as visible in the endoscope's field of view), which creates challenges with respect to hand-eye coordination when using ultrasound images.

By allowing for a 3D visualization using 2D images such as the 2D ultrasound slices, the technology described herein may reduce the challenges associated with using the ultrasound modality in MIS. By displaying the 2D slices concurrently and oriented with respect to one another, the 3D visualization can be implemented without using 3D reconstruction processes that may be too computationally intensive and/or time consuming to be implemented in real time for a fast-paced surgical procedure. In some implementations, by registering the ultrasound images with respect to an image of a different modality (e.g., an endoscope image), the hand-eye coordination issues associated with using ultrasound images in MIS may be mitigated. In some implementations, by registering the ultrasound images with respect to images of a different modality (e.g., a preoperative Computer Tomography (CT) image, Positron Emission Tomography-CT (PET-CT), Magnetic Resonance Imaging (MRI) or a Cone-beam CT (CBCT) image), additional contextual information can be provided to help the surgeon with intraoperative decision making. Overall, the technology described herein may provide a better user-experience for MIS surgeons.

In some implementations, the main visual feedback during MIS is provided via a non-ultrasound modality such as an endoscope image. Additional feedback may be provided, for example, using a different modality such as ultrasound. In some implementations, ultrasound probes (e.g., the probe 400 or 450) can provide 2D image slices of the tissue they are in touch with. For example, a surgeon can obtain the ultrasound images by making a probe traverse a trajectory within the surgical site (e.g., a body part of a patient). In some implementations, the acquired images may be geotagged with location information (e.g., position and orientation with respect to the origin of a known coordinate system). In such cases, the acquired images may be aligned with respect to an underlying image (e.g., an endoscope image) based on the location information associated with the individual images. The alignment can be calculated via an image registration process that includes transforming the sets of data corresponding to the acquired images into one coordinate system based on location information corresponding to the images. This can also be referred to as warping, and can include various rigid or non-rigid transformations such as translation, rotation, shear etc.

Figure 5A:
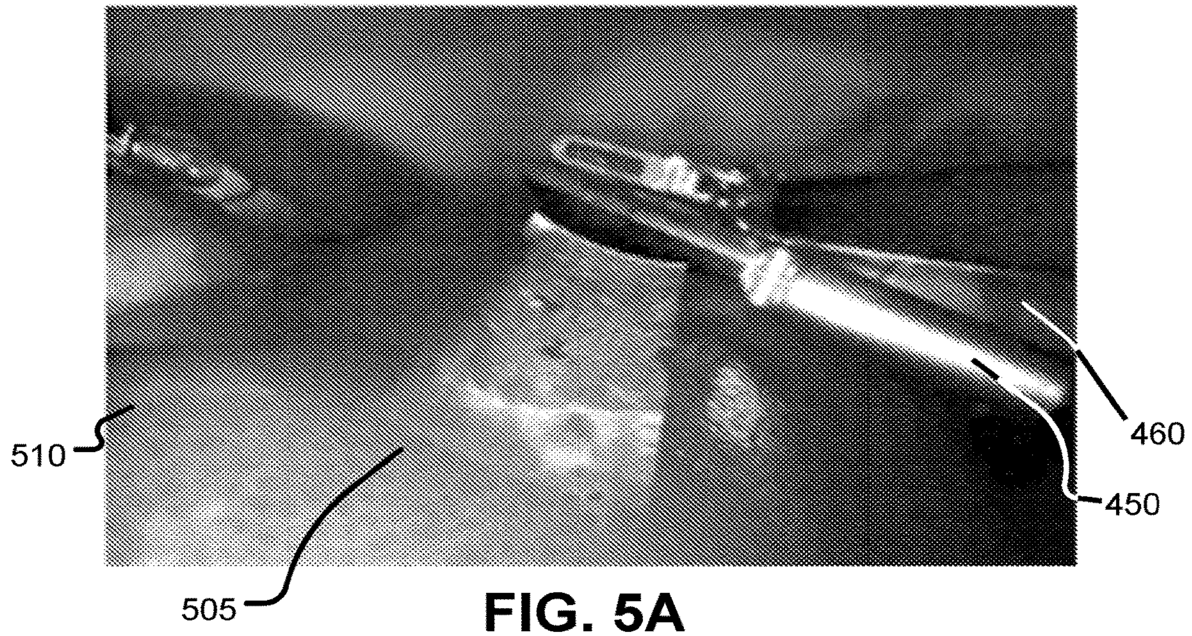
FIGS. 5A and 5B are examples illustrating an ultrasound image registered on an endoscope image.

In some implementations, an acquired ultrasound image can be warped and displayed on an endoscopic image such that the warped image represents the underlying region of the corresponding portion of the endoscopic image. This is illustrated in the example of FIG. 5A, which shows an ultrasound image 505 registered on an endoscope image 510. Due to the shape of the ultrasound image 505, such an ultrasound image can be referred to as being in a "flag-pole" configuration. Other types of ultrasound image configurations may also be used. In some implementations, such warping and displaying of the ultrasound image registered with respect to the endoscope image also positions the ultrasound image in correct alignment with respect to the probe 450 and laparoscopic tool 460 used in acquiring the ultrasound image. In some cases, such alignment with respect to the surgical tools may improve the hand-eye coordination with respect to the ultrasound image.

Figure 5B:
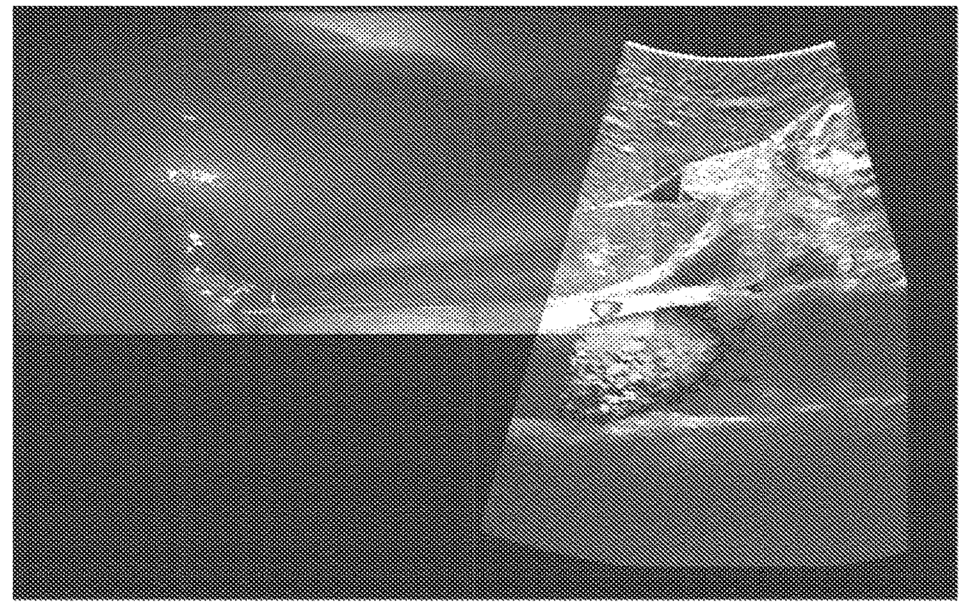

In some cases, the image plane of an ultrasound image may be substantially orthogonal (or near-orthogonal) to the endoscopic image plane. In such cases, an ultrasound image may be displayed as a line, or as a plane with small area, such that content of the ultrasound image is not adequately visible. In such cases, alternative display modes that address the associated challenges may be used. For example, the ultrasound image can be displayed in a planar picture-in-picture mode, but interactive display modes such as vertical or horizontal flipping can be made available, for example, to help with hand-eye coordination. This is illustrated in the example of FIG. 5B, where the ultrasound image is flipped horizontally and shown as a picture-in-picture, to help with hand-eye coordination. In some implementations, a transition from the original image to the warped version may be displayed (e.g., via an animation). In some implementations, such a display mode may be activated in response to a user-input, for example, to provide a better understanding of orientation.

Figure 5C:
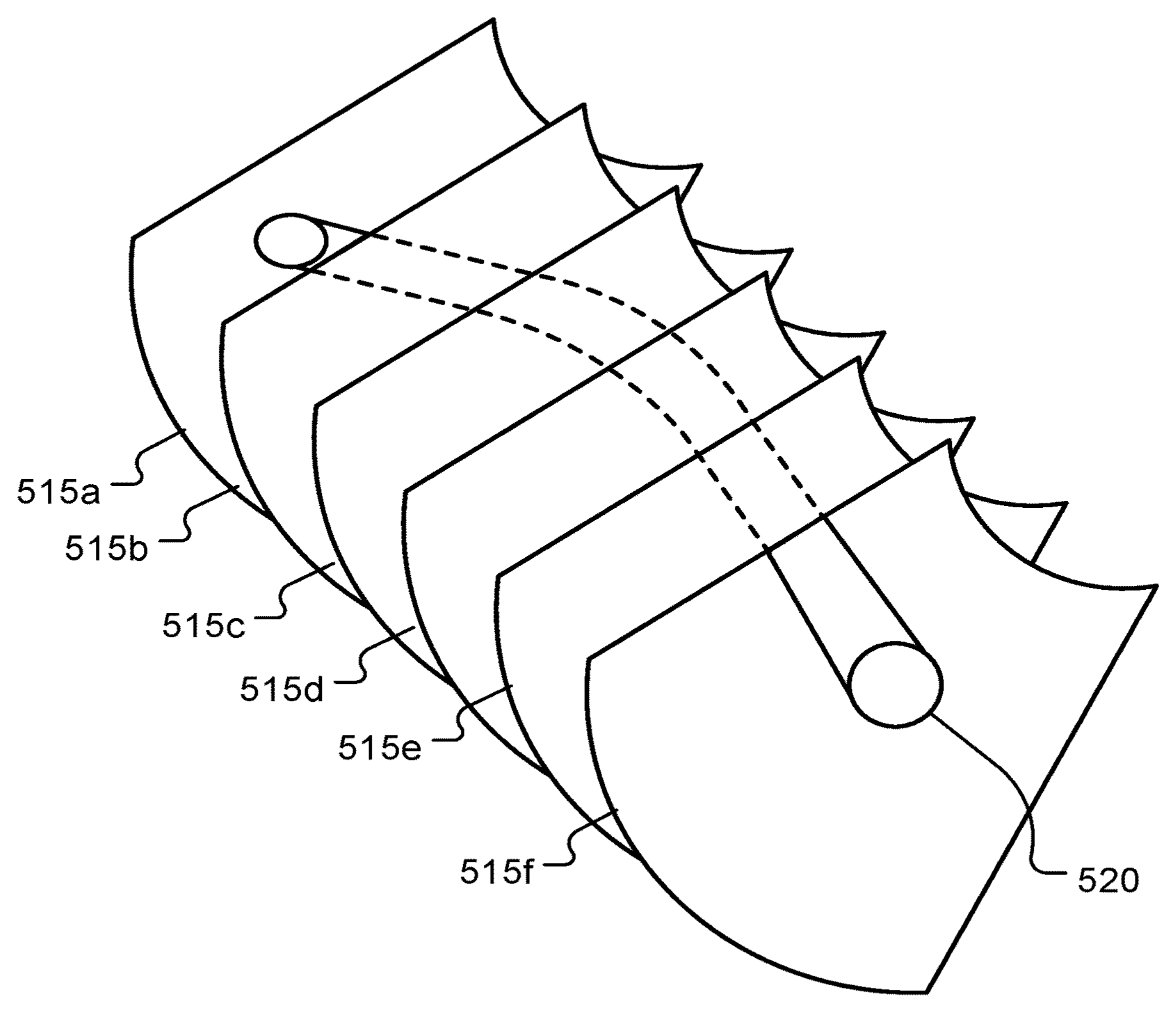
FIG. 5C shows a representation of a 3D visualization based on multiple 2D images.

In some implementations, a series of ultrasound images can be displayed concurrently to provide a 3D visualization with respect to the ultrasound images. For example, if the surgeon moves the ultrasound probe over an area to collect multiple 2D slices over that angle area, at least some of the multiple 2D slices can be displayed (each appropriately warped) concurrently to provide a 3D visualization of the underlying anatomical features. This is illustrated in FIG. 5C, where multiple ultrasound image frames 515*a*-515*f* (515 in general) are displayed in their corresponding acquisition pose and the shape of a blood vessel 520 can be visualized in three dimensions as a result. The sequence or trail of 2D slices can be displayed in various ways based on, for example, user preferences and/or the phase of surgical procedure in progress. In some implementations, warped flag-pole ultrasound images can be displayed as an overlay on another image. An example of such a mode is shown in FIG. 5A, which may be useful in improving hand-eye coordination for the surgeon. In some implementations, only the boundaries of the flag-pole ultrasound images are displayed on the other image (e.g., endoscopic image), while the ultrasound images themselves are displayed at another location (e.g., in a separate window) on the display device.

The 3D visualization can be displayed from various points of view. In some implementations, the point of view can be the location of the endoscope camera. The point of view may be changed (e.g., interactively, based on user-input) to enable viewing of the 3D volume from different locations and poses. For example, the location of the camera may be changed to visualize the displayed 3D volume from various locations. In some implementations, a separate instrument (which may be a real instrument or a virtual or ghost instrument) can be activated, for example based on user-input, to change the point of view for visualizing the displayed 3D volume. Additional controls for interacting with the displayed 3D volume can also be provided. For example, the controls available to the surgeon can include a virtual tool that enables the surgeon to cut through the displayed 3D ultrasound volume to see deeper structures that may be occluded by external structures of the volume. In another example, another virtual tool can enable the surgeon to control a cut plane to crop an image.

Figure 6:
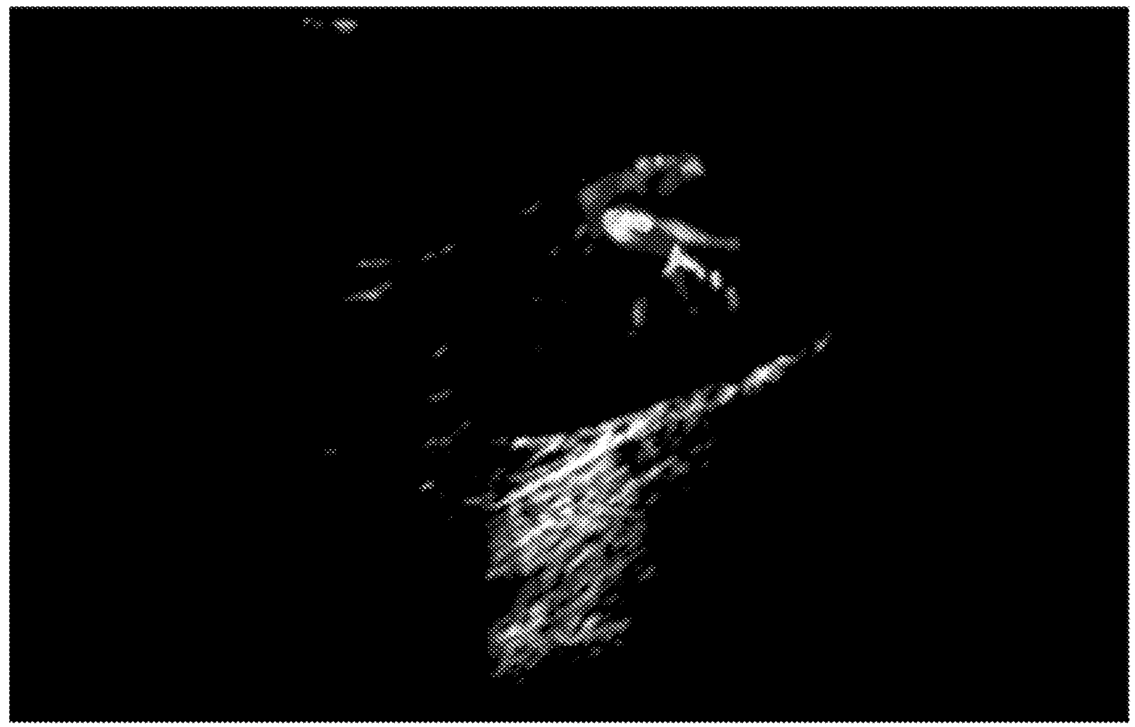
FIG. 6 is an example illustrating a series of colored ultrasound Doppler images registered on a B-mode ultrasound image.

In some implementations, temporal information such as blood flow through vasculature can also be displayed using a series of images. For example, a series of colored Doppler ultrasound images can be displayed in sequence, with at least some of the images in the sequence displayed concurrently, to provide visualization of blood flow. FIG. 6 shows an example where a series of colored ultrasound Doppler images is registered on a B-mode ultrasound image. Specifically, the images in the FIG. 6 were obtained by sweeping an ultrasound probe along the surface of a porcine kidney. The color Doppler images were enabled to visualize vasculature, and a trail of the color Doppler images were displayed registered to a B-mode ultrasound image. The B-mode ultrasound image was used as a reference to interpret the content of the series of color Doppler images.

Figure 7:
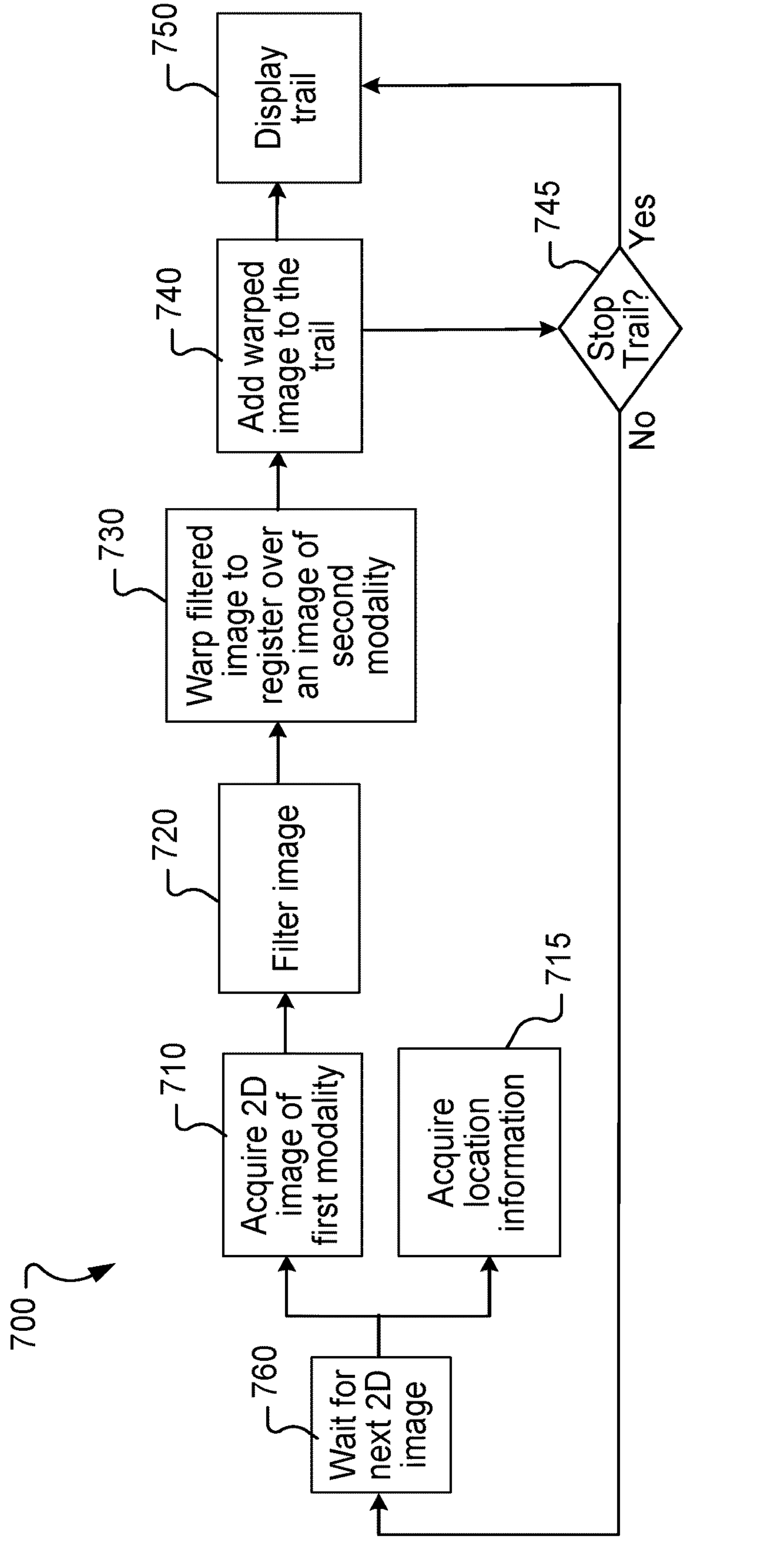
FIG. 7 is a flowchart illustrating an example process of displaying a series of images of one modality on another image of a different modality.

In some implementations, ultrasound images in a sequence are filtered, for example to remove speckle noise, prior to displaying a trail of images from the sequence. In some cases, this can be helpful in avoiding occlusion when multiple images are displayed concurrently. FIG. 7 is a flowchart illustrating an example process 700 that employs filtering while displaying a series of images of one modality on another image of a different modality. In some implementations, at least a portion of the process 700 may be executed by a processing device associated with a surgeon's console of a robotic surgical system. Operations of the process 700 can include acquiring a 2D image of a first modality (710). This can include, for example, receiving a representation of a 2D image of a portion of a human body on which surgery is being performed. In some implementations, the first modality can be ultrasound, wherein the 2D image is one of a plurality of images obtained by sweeping an ultrasound probe over the portion of the human body. Operations of the process 700 also includes acquiring location information (715) for the 2D image. The location information can be represented as, for example, a pose of the ultrasound probe with respect to a known reference point such as the point of view of an endoscope being used in the surgery. In some implementations, the endoscope image can be replaced with the image of a second modality (e.g., Computed Tomography (CT) images) on which one or more images of the first modality are overlaid. In some implementations, the endoscope image can be removed to make the ultrasound images more visible.

Operations of the process 700 further includes filtering the 2D image (720). Various types of spatial or temporal filters can be used for filtering the image. If the 2D image is a B-mode ultrasound image, the filtering can include highlighting boundaries of features (e.g., via edge detection) and/or suppressing noise such as background noise or speckle noise. If the 2D image is a colored Doppler image, the filtering can include removing grayscale content and preserving the color content of the image. In some implementations, noisy color content (e.g., noise due to motion of probe) can also be filtered out. In some implementations, additional filtering may also be performed, for example based on direction of flow, to distinguish between venous flows and arterial flows.

In some implementations, filtering the 2D image (720) can include temporal filtering. The temporal filtering may also be applied in addition to spatial filtering. In some implementations, where the ultrasound probe is swept over an anatomical part or other body part slowly (e.g., at a speed of 1 mm/s), and ultrasound images are captured at a high rate (e.g., 30 frames per second), there may exist a correlation between consecutive ultrasound images. Such correlations can be used to apply temporal filters that may improve visualization of the trail of ultrasound images. In some cases, the temporal filtering may be applied when the spatial distance between two consecutive frames (as determined by the corresponding location information) is less than a threshold value. The threshold value may be determined, for example, from an estimate of the ultrasound image slice thickness determined through a calibration process, or provided by the probe manufacturer.

Operations of the process 700 further includes warping the filtered image to register over an image of a second modality (730). The warping can be performed via an image registration process based on the location information associated with the images of the first and second modality. The location information can include geotagging information with respect to a common coordinate system. Various combinations of first and second modality are possible. For example, the first modality can be ultrasound, and the second modality can be endoscope. In other examples, the first and second modalities can include images acquired using at least two of an endoscope, an ultrasound imaging device, a computed tomography (CT) imaging device, a Positron Emission Tomography-CT (PET-CT) imaging device, a Magnetic Resonance Imaging (MRI) device or a Cone-beam CT (CBCT) imaging device.

Operations of the process 700 further includes adding the warped image to a sequence or trail of images (740) and displaying the trail (750) on a display device. In some implementations, a decision (745) can be made on whether or not to stop adding more images to the trail. If more images are to be added, the operations of the process 700 can include waiting for the next 2D image (760) and repeating the above-noted steps.

Figure 8:
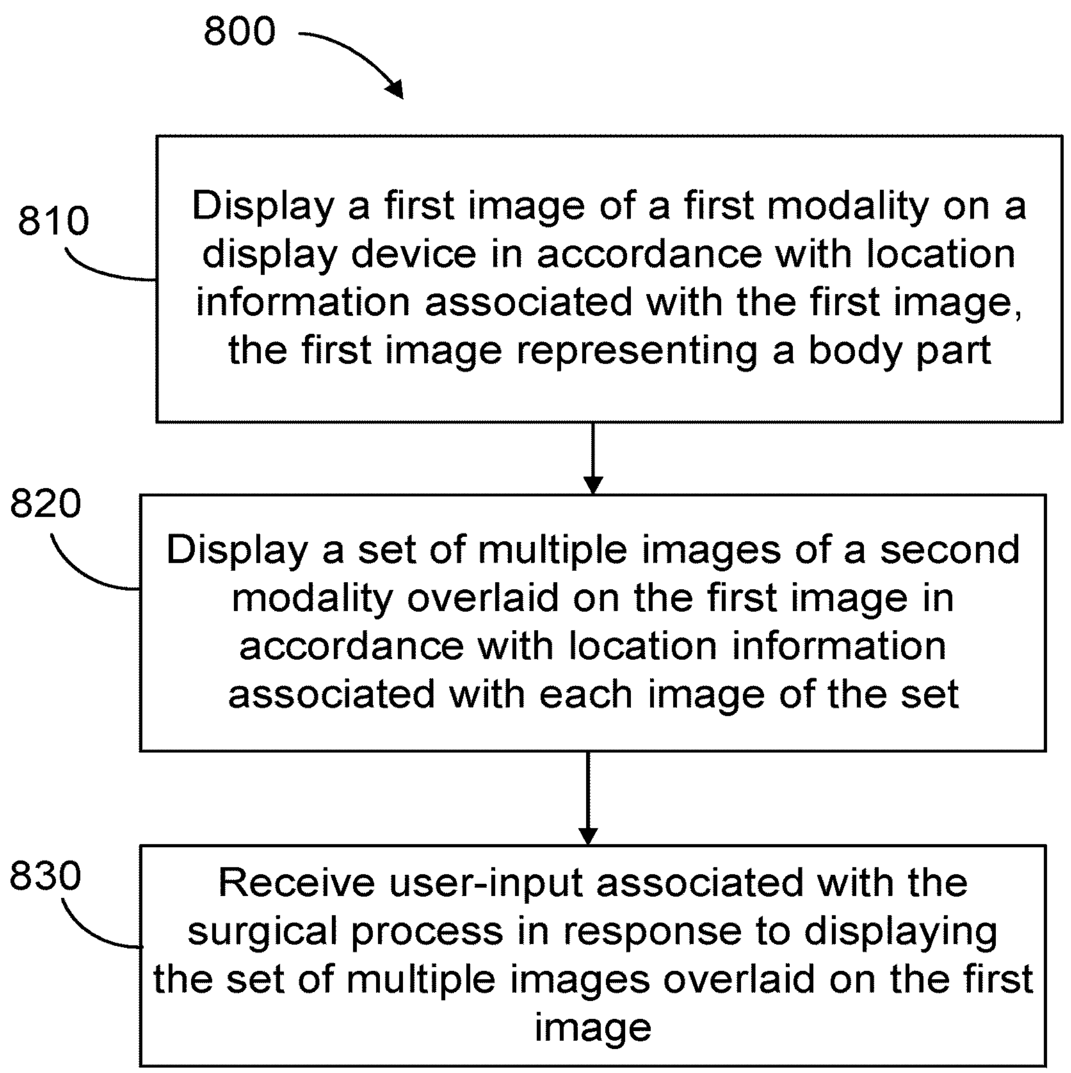
FIG. 8 is a flowchart illustrating an example process of providing feedback and receiving user-input during a surgical process.

FIG. 8 is a flowchart illustrating an example process 800 of providing feedback and receiving user-input during a surgical process. In some implementations, at least a portion of the process 800 may be executed by a processing device associated with a surgeon's console of a robotic surgical system. Operations of the process includes displaying a first image of a first modality on a display device in accordance with location information associated with the first image (810). The first image can represent a body part or anatomical portion where a surgery is being performed. In some implementations, the first image is an endoscopic image, and the corresponding location information includes geotagging information about the imaged location with respect to a predetermined reference point (e.g., location of the endoscope camera). In some implementations, the first image can correspond to another modality such as an image acquired using an ultrasound imaging device, a computed tomography (CT) imaging device, a nuclear imaging device, a radiography imaging device, or a magnetic resonance imaging (MRI) device.

Operations of the process 800 also includes displaying a set of multiple images of a second modality overlaid on the first image in accordance with location information associated with each image of the set (820). The second modality can be different from the first modality. In some implementations, where the first image is an endoscope image, the set of multiple images can be ultrasound images (e.g., B-mode ultrasound images or Doppler ultrasound images). The set of multiple images may be acquired using a probe of an imaging device traversing a trajectory within a surgical site (e.g., a body part, anatomical feature etc.)

In some implementations, at least some of the images from the set of multiple images may be displayed concurrently. For example, if the set of multiple images represent 2D ultrasound slices of a volume of an anatomical feature, at least some of the 2D ultrasound slices can be displayed concurrently to generate a 3D visualization of at least a portion of the anatomical feature. The images from the set can be displayed registered with respect to the first image based on the location information associated with the images from the set. In some implementations, this can include detecting that a new image has replaced the first image, and responsive to such detection adjusting the display of the images from the set in accordance with the location information associated with the new image. For example, if the view of an endoscope image is changed during surgery, a set of 2D ultrasound slices displayed registered to the endoscope image are adjusted accordingly to accommodate the new endoscope image. This can include, for example, registering the images from the set with respect to the new image.

Operations of the process 800 further includes receiving user input associated with the surgical process in response to displaying the set of multiple images overlaid on the first image (830). The user input can include instructions to move a physical tool associated with a robot-assisted image-guided surgery system. For example, based on visualizing the location of a tumor based on a set of ultrasound images displayed as an overlay on an endoscopic image, a surgeon may activate a tool to make an incision to excise the tumor with a margin around the tumor. The user-input can also include instructions to change an angle of visualization and/or instructions to activate a virtual tool. For example, a surgeon can change a viewpoint to visualize the set of images from a different location. Also, the virtual tool may allow a surgeon to make a virtual incision in the displayed volume, for example to better understand the location/nature of the tumor. In some cases, this may allow the surgeon to better assess a situation before initiating an actual surgical operation.

In some implementations, the various types of trail visualization described above may be improved by applying motion constraints on the robotic arm (e.g., a robotic arm manipulator assembly 120 described above) that holds an imaging transducer. For example, in robot-assisted MIS, tracking of ultrasound probes held by a robotic arm can be improved (e.g., as compared to manual laparoscopic procedures), for example, via tracking of the robotic arm using joint encoders and/or kinematic calculations. Various techniques may be used for controlling the robotic arm. In some implementations, virtual viscosity and motion damping may be applied to an arm holding an imaging transducer such as an ultrasound probe. This may result in slower or smoother motion, which in turn may provide better trail visualization. In some implementations, the control mechanism for the arm may include a force sensor that can be operated under a motion constraint, for example, to maintain a constant contact force between an imaging transducer (e.g., an ultrasound probe) and an anatomical feature (e.g., soft tissue) at the surgical site. In some cases, image processing techniques may be used to discard frames obtained during a period when the transducer is not in full contact with the anatomical feature. In some implementations, user-input indicative of a desired trajectory of a probe may be recorded, and a robotic arm may be made to traverse the trajectory in a smooth motion (e.g., at a constant speed).

The functionality described herein, or portions thereof, and its various modifications (hereinafter "the functions") can be implemented, at least in part, via a computer program product, e.g., a computer program tangibly embodied in an information carrier, such as one or more non-transitory machine-readable media or storage device, for execution by, or to control the operation of, one or more data processing apparatus, e.g., a programmable processor, a DSP, a microcontroller, a computer, multiple computers, and/or programmable logic components.

A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one or more processing devices at one site or distributed across multiple sites and interconnected by a network.

Actions associated with implementing all or part of the functions can be performed by one or more programmable processors or processing devices executing one or more computer programs to perform the functions of the processes described herein. All or part of the functions can be implemented as, special purpose logic circuitry, e.g., an FPGA and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. Components of a computer include a processor for executing instructions and one or more memory devices for storing instructions and data.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical system comprising:

a display device; and one or more processing devices configured to:

receive a plurality of two-dimensional (2D) images of portions of a human body, wherein the plurality of 2D images includes images acquired using at least two different imaging modalities;

display a first image of the plurality of 2D images on the display device in accordance with location information associated with the first image, the first image being acquired using a first imaging modality;

display a second image of the plurality of 2D images, the second image overlaid on and registered with respect to the first image in accordance with the location information associated with the second image, the second image being acquired using a second imaging modality; and display at least a third image of the plurality of 2D images, the third image overlaid on and registered with respect to the first image in accordance with the location information associated with the third image, the third image being acquired using the second imaging modality;

wherein the second image and the third image are displayed together for at least a period of time.

2. The surgical system of claim 1, wherein the one or more processing devices are configured to display the first image in a hidden mode such that the first image is not visible.

3. The surgical system of claim 1, wherein:

the first image is a 2D B-mode ultrasound image; and the second image and the third image are 2D Doppler ultrasound images.

4. The surgical system of claim 1, wherein:

the first image is an endoscopic image; and the second image and the third image are ultrasound images.

5. The surgical system of claim 1, wherein the one or more processing devices are further configured to cause a probe of an imaging device to traverse a trajectory within the human body.

6. The surgical system of claim 5, further comprising:

a robotic arm configured to hold the imaging device;

wherein the one or more processing devices are further configured to apply at least one motion constraint to the robotic arm when causing the probe to traverse the trajectory within the human body.

7. The surgical system of claim 1, wherein:

at least one of the two different imaging modalities comprises live images acquired using at least one of an endoscope or an ultrasound imaging device; and the other of the two different imaging modalities comprises images acquired using at least one device selected from a group consisting of: an endoscope, an ultrasound imaging device, a computed tomography (CT) imaging device, a Positron Emission Tomography-CT (PET-CT) imaging device, a Single-Photon Emission CT (SPECT) imaging device, a Magnetic Resonance Imaging (MRI) device, and a Cone-beam CT (CBCT) imaging device.

8. The surgical system of claim 1, wherein the location information associated with the first image, the second image, and the third image includes geo-tagging information with respect to a common coordinate system.

9. The surgical system of claim 1, wherein the second image and the third image are registered with respect to the first image or with respect to a common reference coordinate system.

10. The surgical system of claim 1, wherein the second image and the third image are acquired at different times.

11. The surgical system of claim 1, wherein:

the one or more processing devices are further configured to:

detect that a new image is being displayed on the display device in place of the first image; and in response to a detection that the new image is being displayed, adjust the display of the second image and the third image in accordance with location information associated with the new image.

12. The surgical system of claim 1, wherein the second image and the third image create a three-dimensional (3D) visualization of the portions of the human body.

13. A method of displaying images of portions of a human body on a display device, the method comprising:

receiving a plurality of two-dimensional (2D) images of the portions of the human body, wherein the plurality of 2D images includes images acquired using at least two different imaging modalities;

displaying a first image of the plurality of 2D images on the display device in accordance with location information associated with the first image, the first image being acquired using a first imaging modality;

displaying a second image of the plurality of 2D images, the second image overlaid on and registered with respect to the first image in accordance with location information associated with the second image, the second image being acquired using a second imaging modality; and displaying at least a third image of the plurality of 2D images, the third image overlaid on and registered with respect to the first image in accordance with location information associated with the third image, the third image being acquired using the second imaging modality;

wherein the second and third images are displayed together for at least a period of time.

14. The method of claim 13, further comprising:

displaying the first image in a hidden mode such that the first image is not visible.

15. The method of claim 13, further comprising:

causing a probe of an imaging device to traverse a trajectory within the human body.

16. The method of claim 13, wherein:

at least one of the two different imaging modalities comprises live images acquired using at least one of an endoscope or an ultrasound imaging device; and the other of the two different imaging modalities comprises images acquired using at least one device selected from a group consisting of: an endoscope, an ultrasound imaging device, a computed tomography (CT) imaging device, a Positron Emission Tomography-CT (PET-CT) imaging device, a Single-Photon Emission CT (SPECT) imaging device, a Magnetic Resonance Imaging (MRI) device, and a Cone-beam CT (CBCT) imaging device.

17. The method of claim 13, wherein the location information associated with the first image, the second image, and the third image includes geo-tagging information with respect to a common coordinate system.

18. The method of claim 13, wherein the second image and the third image are registered with respect to the first image or with respect to a common reference coordinate system.

19. The method of claim 13, further comprising:

detecting that a new image is being displayed on the display device in place of the first image; and in response to detecting that the new image is being displayed, adjusting the display of the second image and the third image in accordance with location information associated with the new image.

20. One or more machine-readable non-transitory storage devices encoded with machine-readable instructions configured to cause one or more processing devices to perform operations comprising:

receiving a plurality of two-dimensional (2D) images of portions of a human body, wherein the plurality of 2D images includes images acquired using at least two different imaging modalities;

displaying a first image of the plurality of 2D images on a display device in accordance with location information associated with the first image, the first image being acquired using a first imaging modality;

displaying a second image of the plurality of 2D images, the second image overlaid on and registered with respect to the first image in accordance with location information associated with the second image, the second image being acquired using a second imaging modality; and displaying at least a third image of the plurality of 2D images, the third image overlaid on and registered with respect to the first image in accordance with location information associated with the third image, the third image being acquired using the second imaging modality;

wherein the second and third images are displayed together for at least a period of time.

* * * * *